(12) United States Patent
Zhang

(10) Patent No.: US 10,173,995 B2
(45) Date of Patent: Jan. 8, 2019

(54) PYRIDINE COMPOUNDS USED AS PI3 KINASE INHIBITORS

(71) Applicant: Dawei Zhang, Thousand Oaks, CA (US)

(72) Inventor: Dawei Zhang, Thousand Oaks, CA (US)

(73) Assignee: Teligene Ltd., Suzhou (CN)

( * ) Notice: Subject to any disclaimer, the term of this patent is extended or adjusted under 35 U.S.C. 154(b) by 0 days.

(21) Appl. No.: 14/760,472

(22) PCT Filed: Jan. 11, 2014

(86) PCT No.: PCT/US2014/011177
§ 371 (c)(1),
(2) Date: Jul. 11, 2015

(87) PCT Pub. No.: WO2014/110466
PCT Pub. Date: Jul. 17, 2014

(65) Prior Publication Data
US 2015/0353524 A1    Dec. 10, 2015

Related U.S. Application Data

(60) Provisional application No. 61/848,790, filed on Jan. 12, 2013.

(51) Int. Cl.
*C07D 401/04* (2006.01)
*A61K 31/5377* (2006.01)
*A61K 45/06* (2006.01)
*A61K 31/5355* (2006.01)

(52) U.S. Cl.
CPC ........ *C07D 401/04* (2013.01); *A61K 31/5355* (2013.01); *A61K 31/5377* (2013.01); *A61K 45/06* (2013.01)

(58) Field of Classification Search
CPC .................................................... C07D 401/04
See application file for complete search history.

(56) References Cited

U.S. PATENT DOCUMENTS

| | | | |
|---|---|---|---|
| 2009/0060912 A1 | 3/2009 | Nuss et al. | |
| 2010/0048547 A1 | 2/2010 | Atallah et al. | |
| 2011/0275762 A1 | 11/2011 | Cmiljanovic et al. | |
| 2014/0275003 A1* | 9/2014 | Barsanti | C07D 403/12 514/210.2 |

FOREIGN PATENT DOCUMENTS

| WO | WO2014/012093 | * | 1/2014 |
| WO | WO 2014/064058 | * | 5/2014 |

* cited by examiner

*Primary Examiner* — Rebecca L Anderson
(74) *Attorney, Agent, or Firm* — Feng Tian

(57) ABSTRACT

The present invention is directed to novel pyridines, their derivatives, pharmaceutically acceptable salts, solvates and hydrates thereof. The present invention discloses compounds of Formulas I and II. The compounds and compositions of the present invention have protein kinases inhibitory activities and are expected to be useful for the treatment of protein kinases mediated diseases and conditions.

1 Claim, No Drawings

PYRIDINE COMPOUNDS USED AS PI3 KINASE INHIBITORS

CROSS REFERENCE

This invention claims the benefits of U.S. Provisional Patent Application No. 61/848,790 filed on Jan. 12, 2013, which is incorporated herein by reference in its entirety.

FIELD OF THE INVENTION

The present invention is directed to inhibitors of PI3 kinases and pharmaceutically acceptable salts, solvates, hydrates, prodrugs and metabolites thereof, the preparation thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Examples of kinases in the protein kinase family include, without limitation, Abl1 (v-Abl Abelson murine leukemia viral oncogene homolog 1), Akt, Alk, Bcr-Abl1, Blk, Brk, Btk, c-Kit, c-Met, c-Src, c-Fms, CDK1-10, b-Raf, c-Raf1, CSF1R, CSK, EGFR, ErbB2, ErbB3, ErbB4, Erk, FGFR1, FGFR2, FGFR3, FGFR4, FGFR5, Flt-1, Fps, Frk, Jak, KDR, MEK, PDGFR, PIK, PKC, PYK2, Ros, Tie, Tie2, and Zap70. Due to their activity in numerous cellular processes, protein kinases have emerged as important therapeutic targets.

PI3 kinases (phosphoinositide 3-kinases, PI3Ks) are family of lipid kinases capable of phosphorylating the 3'-OH of the inositol ring of phosphoinositides. The phosphoinositol-3-kinase family is divided into three different classes: Class I, Class II, and Class III. The classifications are based on primary structure, regulation, and in vitro lipid substrate specificity. PI3 kinases are responsible for coordinating a diverse range of cell functions including proliferation, cell survival, degranulation, vesicular trafficking and cell migration, which in turn are involved in cancer.

To this end, attempts have been made to identify small molecules which act as PI3 kinases inhibitors. For example, pyrimidine derived compounds (international patent applications WO2007084786 and WO2008098058) have been described as PI3 kinases inhibitors.

Thus, the compounds that can inhibit protein kinases such as PI3 and other kinases activity either independently or together can be used to treat human diseases such as cancers.

SUMMARY OF THE INVENTION

The present invention provides compounds of Formula I:

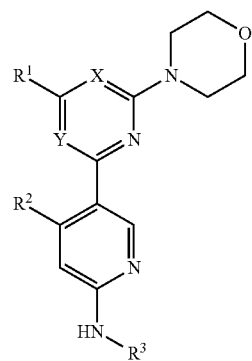

I or a pharmaceutically acceptable salt, solvate or a prodrug or an enantiomer, or a metabolite thereof, wherein $R^1$ is hydrogen, $C_1$-$C_6$ alkyl, hydroxy, amino, N-methylamino, N,N-dimethylamino, $C_6$-$C_{12}$ aryl, 3-12 membered heteroalicyclic, or 5-12 membered heteroaryl;

$R^2$ is hydrogen, $C_1$-$C_6$ alkyl, $C_1$-$C_6$ alkoxy, trifluoromethyl, cyano, or hydroxy;

$R^3$ is $C_1$-$C_6$ alkyl, —C(O)$R^4$, —SO$_2R^4$, or —C(O)O$R^5$;

$R^4$ is $C_1$-$C_6$ alkyl; $C_1$-$C_6$ alkyl substituted by one or more of halogen, deuterium, or hydroxyl; $C_6$-$C_{12}$ aryl; 3-12 membered heteroalicyclic; 5-12 membered heteroaryl; or a residue of amino acid;

$R^5$ is $C_1$-$C_6$ alkyl, $C_1$-$C_6$ alkyl substituted by $C_1$-$C_6$ acyloxy, or 3-12 membered heteroalicyclic;

Y is N or CH; and

X is N when Y is CH, and X is CH when Y is N.

The present invention further provides pharmaceutical compositions comprising a compound of Formula I described above and a pharmaceutically acceptable carrier.

The present invention further provides methods for treating or preventing a PI3 kinases mediated disorder comprising administrating to a mammalian subject a therapeutically effective amount of any of the compounds of Formula I described above.

DETAILED DESCRIPTION OF THE INVENTION

In some embodiments of the present invention, there are provided compounds of Formula I:

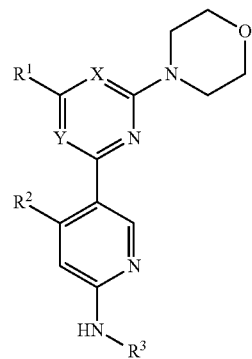

I or a pharmaceutically acceptable salt, solvate or an enantiomer, or a prodrug or a metabolite thereof, wherein $R^1$ is hydrogen, $C_1$-$C_6$ alkyl, hydroxy, amino, N-methylamino, N,N-dimethylamino, $C_6$-$C_{12}$ aryl, 3-12 membered heteroalicyclic, or 5-12 membered heteroaryl;

$R^2$ is hydrogen, $C_1$-$C_6$ alkyl, $C_1$-$C_6$ alkoxy, trifluoromethyl, cyano, or hydroxy;

$R^3$ is $C_1$-$C_6$ alkyl, —C(O)$R^4$, —SO$_2$$R^4$, or —C(O)O$R^5$;

$R^4$ is $C_1$-$C_6$ alkyl; $C_1$-$C_6$ alkyl substituted by one or more of halogen, deuterium, or hydroxyl; $C_6$-$C_{12}$ aryl; 3-12 membered heteroalicyclic; 5-12 membered heteroaryl; or a residue of amino acid;

$R^5$ is $C_1$-$C_6$ alkyl, $C_1$-$C_6$ alkyl substituted by $C_1$-$C_6$ acyloxy, or 3-12 membered heteroalicyclic;

Y is N or CH; and

X is N when Y is CH, and X is CH when Y is N.

In certain embodiments, the invention provides for compounds of Formula I wherein $R^1$ is morpholino.

In other embodiments, the invention provides for compounds of Formula I wherein $R^2$ is a trifluoromethyl.

In some embodiments, the invention provides for compounds of Formula I wherein $R^3$ is —C(O)CH$_3$.

In some embodiments, the invention provides for compounds of Formula I wherein X is N and Y is CH, $R^1$ is -morpholino, $R^2$ is —CF$_3$, and $R^3$ is $C_1$-$C_6$ alkyl.

In other embodiments, the invention provides for compounds of Formula I wherein $R^3$ is —C(O)CH$_2$NH$_2$.

In some embodiments of the present invention, there are provided compounds of Formula II:

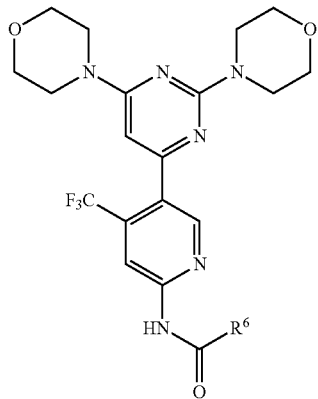

II or a pharmaceutically acceptable salt, solvate or a prodrug or a stereoisomer or a tautomer or a metabolite thereof, wherein $R^6$ is $C_1$-$C_6$ alkyl; $C_1$-$C_6$ alkyl substituted by one or more of halogen, deuterium, or hydroxyl; $C_1$-$C_6$ alkoxy; $C_1$-$C_6$ alkoxy substituted by acyloxy; $C_6$-$C_{12}$ aryl; or a residue of amino acid.

In certain embodiments, the invention provides compounds of Formula II wherein $R^6$ is methyl.

In other embodiments, the invention provides compounds of Formula II wherein $R^6$ is —CH$_2$NH$_2$.

In some embodiments, the invention provides compounds of Formula II wherein $R^6$ is —OCH$_2$CH$_3$.

In certain representative embodiments, there are provided compounds without limitation selected from the group consisting of:

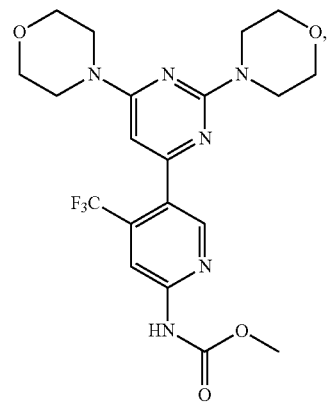

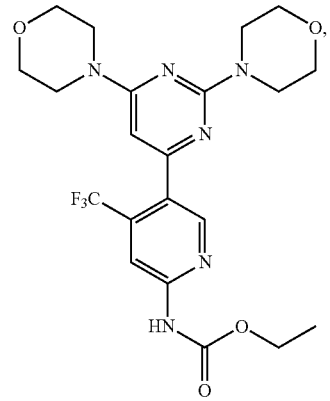

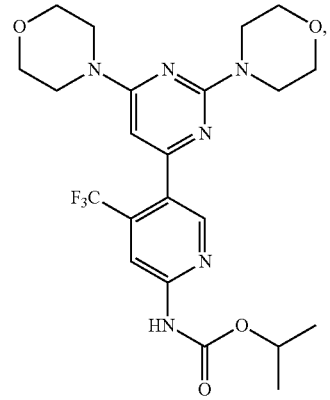

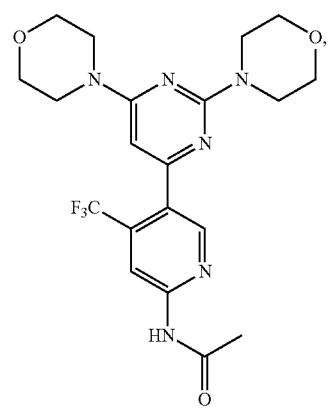

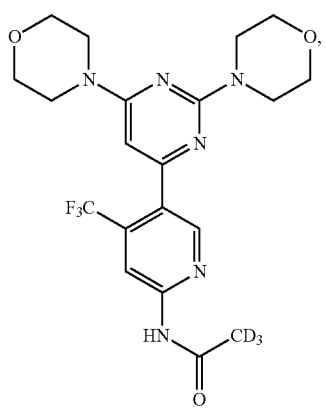
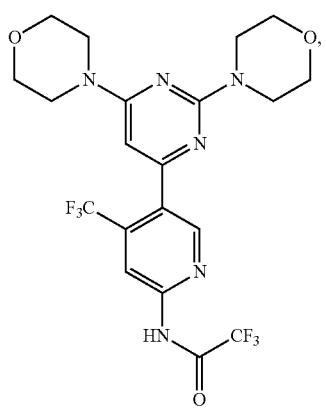
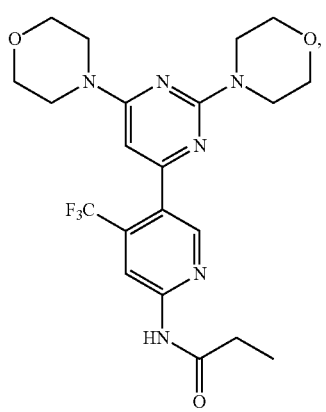
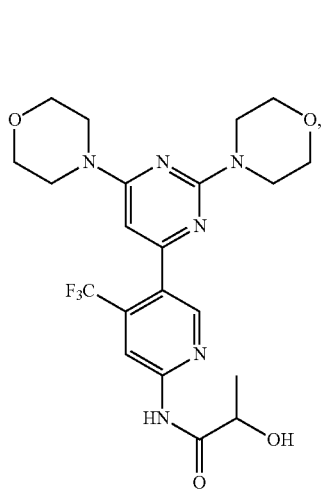
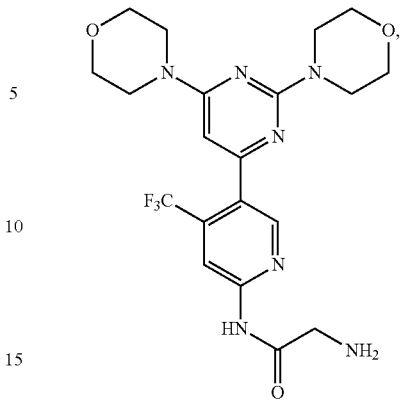
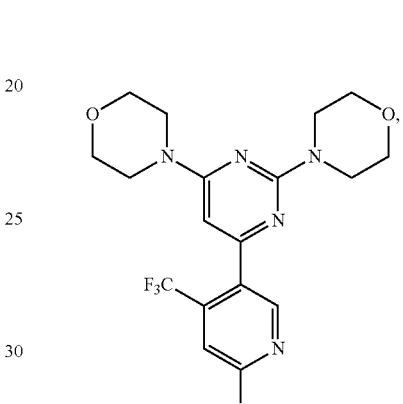
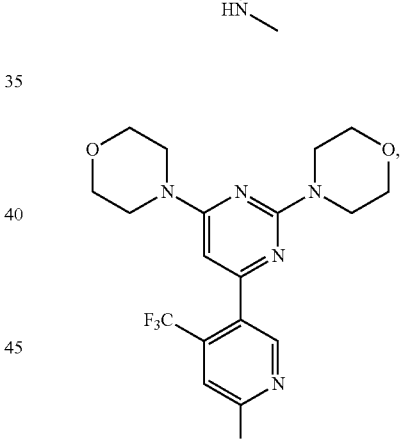
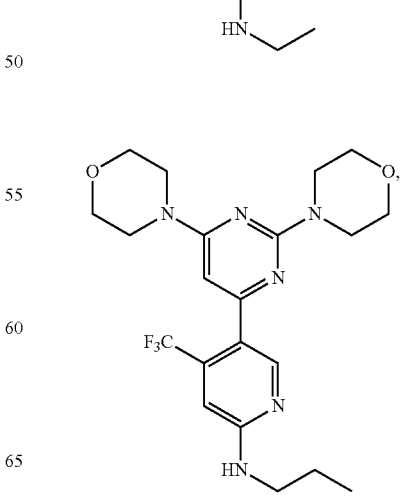

-continued
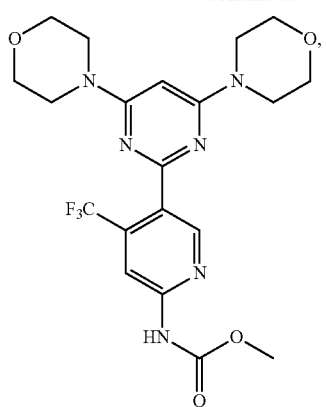
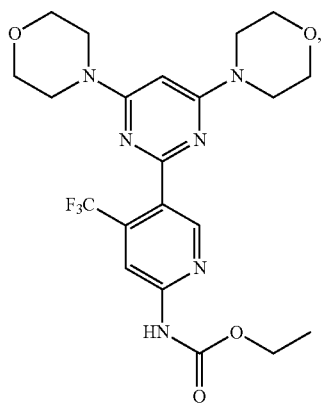
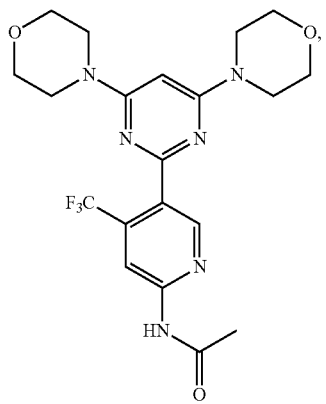
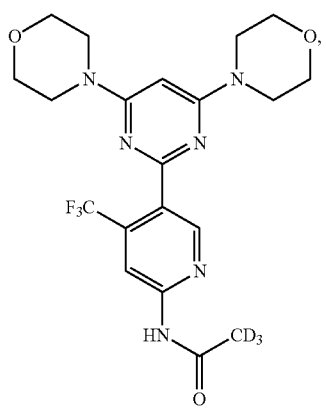
-continued
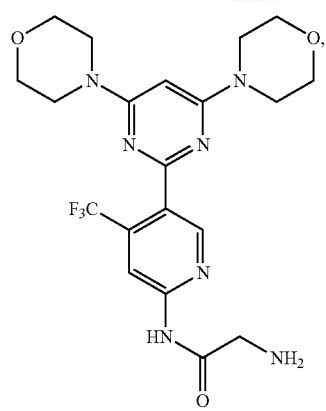
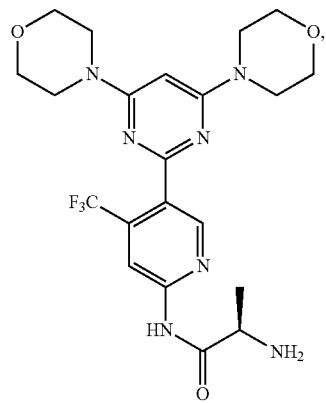
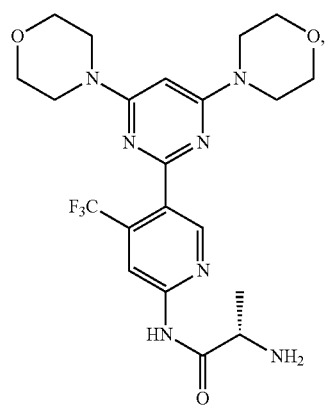
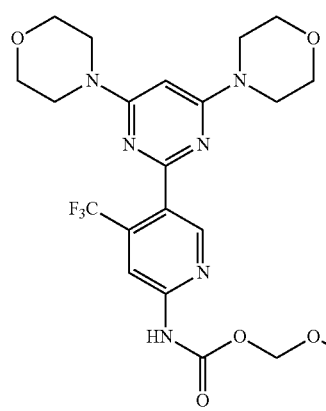

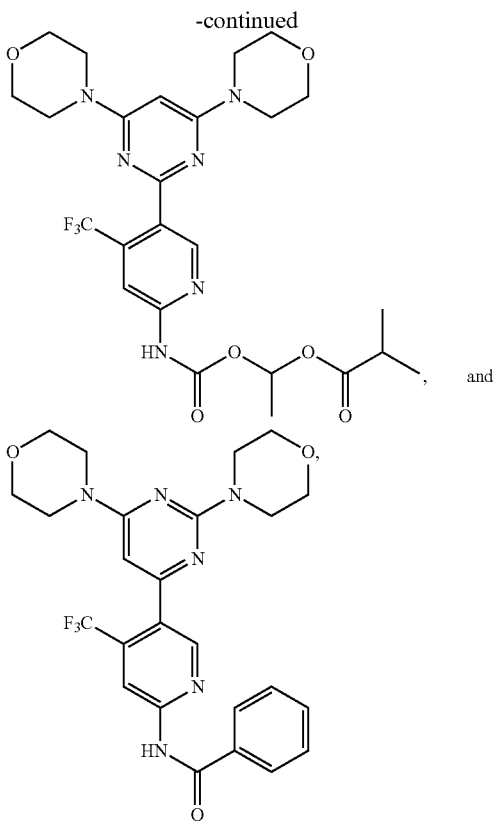

or a pharmaceutically acceptable salt, solvate, or a prodrug, or a metabolite thereof.

In other embodiments, the compound of this invention is in the form of pharmaceutically acceptable salt. In some embodiments, the compound of this invention is in the form of a solvate. In other embodiments, the compound of this invention is in the form of a metabolite. In other embodiments, the compound of this invention is in the form of a prodrug. In some embodiments, the compound of this invention is an enantiomer. In other embodiments, the compound of this invention is a diastereomer. In another embodiment, the deuterium enrichment in compounds of this invention is at least about 1%.

In some embodiments, there are provided pharmaceutical compositions comprising a compound of the invention and a pharmaceutically acceptable carrier. In certain embodiments, the compositions are for the treatment of a disease regulated by a protein kinase. In certain embodiments, the compositions are for the prevention or the treatment of a hyper-proliferative disorder and/or angiogenesis disorder. In some embodiments, the pharmaceutical compositions further comprise an anti-neoplastic agent, an immunosuppressant, an immunostimulant, or combination thereof. In other embodiments, the pharmaceutical compositions are suitable for oral, parenteral, or intravenous administration.

In some embodiments, the present invention provides methods for regulating the kinase signaling transduction comprising administrating to a mammalian subject a therapeutically effective amount of any of the inventive compounds described herein.

In other embodiments, there are provided herein methods for treating or preventing a PI3 kinases mediated disorder, said method comprises administrating to a mammalian subject a therapeutically effective amount of any of the inventive compounds described herein.

In other embodiments, there are provided herein methods for treating neoplasia comprising administrating to a mammalian subject in need thereof, a therapeutically effective amount of any of the inventive compounds described herein. In certain embodiments, the neoplasia is selected from skin cancer, leukemias, colon carcinoma, renal cell carcinoma, gastrointestinal stromal cancer, solid tumor cancer, myeloma, breast cancer, pancreatic carcinoma, non-small cell lung cancer, non-Hodgkin's lymphoma, hepatocellular carcinoma, thyroid cancer, bladder cancer, colorectal cancer, and prostate cancer. In some embodiments, the methods further comprise administering one or more anti-cancer agents.

In other embodiments, there are provided methods for treating or preventing a hyper-proliferative and/or angiogenesis comprising administrating to a mammalian subject a therapeutically effective amount of any of the inventive compounds described herein.

The following definitions should assist in understanding the invention described herein.

The term "alkyl" is intended to include straight, branched, and cyclic hydrocarbon groups, which contain only single carbon-carbon bonds and which may be unsubstituted or optionally substituted with one or more functional groups. The preferred chain length of an alkyl group is from 1 to 6 carbon atoms. $C_1$-$C_6$ alkyl is intended to include $C_1$, $C_2$, $C_3$, $C_4$, $C_5$ and $C_6$ alkyl groups. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^XR^Y$, wherein $R^X$ and $R^Y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring. Illustrative substituted alkyl group include, but are not limited to, fluoromethyl, difluoromethyl, trifluoromethyl, aminomethyl, aminoethyl, hydroxymethyl, methoxymethyl, 2-fluoroethyl, and 2-methoxyethyl, etc.

The term "alkoxy" refers to both an —O-(alkyl) and an —O-(unsubstituted cycloalkyl) group. $C_1$-$C_6$ alkoxy is intended to include $C_1$-$C_6$ alkyl groups, wherein $C_1$-$C_6$ alkyl is defined above. Representative examples include, but are not limited to, methoxy, ethoxy, propoxy, butoxy, cyclopropyloxy, cyclobutyloxy, cyclopentyloxy, cyclohexyloxy, and the like.

"Aryl" refers to an all-carbon monocyclic or fused-ring polycyclic groups of 6 to 12 carbon atoms having a completely conjugated π-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^XR^Y$, with $R^X$ and $R^Y$ as defined above.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrazine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —NR$^X$R$^Y$ with R$^X$ and R$^Y$ as defined above. A pharmaceutically acceptable heteroaryl is one that is sufficiently stable to be attached to a compound of the invention, formulated into a pharmaceutical composition and subsequently administered to a patient in need thereof.

"Heteroalicyclic" or "heterocycle" refers to a monocyclic or fused ring group having in the ring(s) of 3 to 12 ring atoms, in which one or two ring atoms are heteroatoms selected from N, O, and S(O)$_t$, (where t is 0, 1 or 2), the remaining ring atoms being C. The rings may also have one or more double bonds. However, the rings do not have a completely conjugated π-electron system. Additionally, one or more of the ring atoms could be substituted by an oxo group. Examples of suitable saturated heteroalicyclic groups include, but are not limited to: tetrahydrofuran, tetrahydrothiophene, pyrrolidine, piperidine, morpholine, and piperazine.

"Halogen" means fluorine, chlorine, bromine, and iodine. "Halo" means fluoro, chloro, bromo, and iodo, preferably fluorine or chlorine.

"Amino acid" means organic compounds composed of amine (—NH$_2$) and carboxylic acid (—COOH) functional groups, along with a side-chain specific to each amino acid. Examples include, but are not limited to, alanine, asparagine, aspartic acid, cysteine, glutamic acid, glutamine, glycine, proline, serine and tyrosine, 3-aminopropanoic acid, and the like.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as deuterium and carbon such as $^{13}$C. Substitution with heavier isotopes such as deuterium may afford certain therapeutic advantages resulting from greater metabolic stability; for example, increased in vivo half-life or reduced dosage requirements, and hence may be preferred in some circumstances.

Deuterium (D or $^2$H) is a non-radioactive, stable isotope of hydrogen, the natural abundance of deuterium is 0.015%. A compound should be considered to be unnatural, if its level of deuterium has been enriched to be greater than the natural abundance level of 0.015%. In a compound of this invention, it is understood that the abundance of deuterium is substantially greater than the natural abundance of deuterium, which is 0.015%, when a particular position is designated as deuterium. A position designated as deuterium typically has a minimum isotopic enrichment factor of at least 3000 at each atom designated as deuterium in said compound. The concentration of naturally abundant stable hydrogen is small and immaterial compared to the degree of stable isotopic substitution of compounds of this invention.

The term "pharmaceutically acceptable" when used with reference to a compound of the invention is intended to refer to a form of the compound that is safe for administration to a subject. For example, a free base, a salt form, a solvate, a hydrate, a prodrug or derivative form of a compound of this invention, which has been approved for mammalian use, via oral ingestion or any other route of administration, by a governing authority or regulatory agency, such as the Food and Drug Administration (FDA) of the United States, is pharmaceutically acceptable.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described below.

In synthesizing a compound of formulas I and II according to a desired procedure, the steps in some embodiment, are performed in an order suitable to prepare the compound, including a procedure described herein or by an alternate order of steps described herein, and in one embodiment, be preceded, or followed, by additional protection/deprotection steps as necessary. The intermediates in some embodiments are isolated or carried on in situ, with or without purification. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Proton NMR Spectra

Unless otherwise indicated, all $^1$H NMR spectra were run on a Varian series Mercury 300, 400, 500 MHz instrument or a Bruker series 400, 500 MHz instrument. Where so characterized, all observed protons are reported as parts-per-million (ppm) downfield from tetramethylsilane (TMS) or other internal reference in the appropriate solvent indicated.

ABBREVIATIONS

DMF means N,N-dimethylformamide.
DCM means dichloromethane.
DIPEA means diisopropyl ethylamine.

THF means tetrahydrofuran.
TEA means triethylamine.
EA means ethyl acetate.
EDC means 1-ethyl-3-(3-dimethylaminopropyl)carbodiimide.
KI means potassium iodine.
NaH means sodium hydride.
RT means room temperature.
Fmoc-glycine means N-(9-fluorenylmethoxycarbonyl)glycine.

Synthesis of Compounds

The compounds of Formulas I and II were synthesized according to the procedures described in the following Schemes to those skilled in the art, wherein the substituents are as defined for Formulas I and II above, except where further noted. The synthetic methods described below are merely exemplary, and the compounds of the invention may also be synthesized by alternate routes as appreciated by persons of ordinary skill in the art.

The synthesis of compounds of Formulas I in the invention was described in the Scheme 1. The synthesis of Compound A has been reported using procedures similar to those described in the literature (WO2007084786, WO2008098058 and WO2010006225). The amino group of Compound A reacts with Compound B under basic condition to generate compounds of Formula I.

Scheme 1

X = Br, I or Cl

An alternative way to synthesize compounds of Formula I is by the palladium catalyzed Suzuki reaction of Compound C and Compound D as described in Scheme 2.

Scheme 2

The synthesis of compounds of Formulas II was described in Scheme 3. The literature known Compound 1 reacted with acyl chloride of Compound E and base such as pyridine to give compounds in Formula II.

Scheme 3

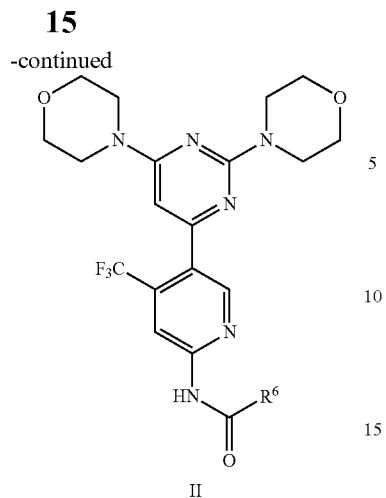

II

The synthesis of Compound 9 was described in Scheme 4. The Fmoc-glycine reacted with thionyl chloride to give Compound 7, which reacted with Compound 1 under basic condition to generate Compound 8. The deprotection of Compound 8 with piperidine led to the synthesis of Compound 9.

Scheme 4

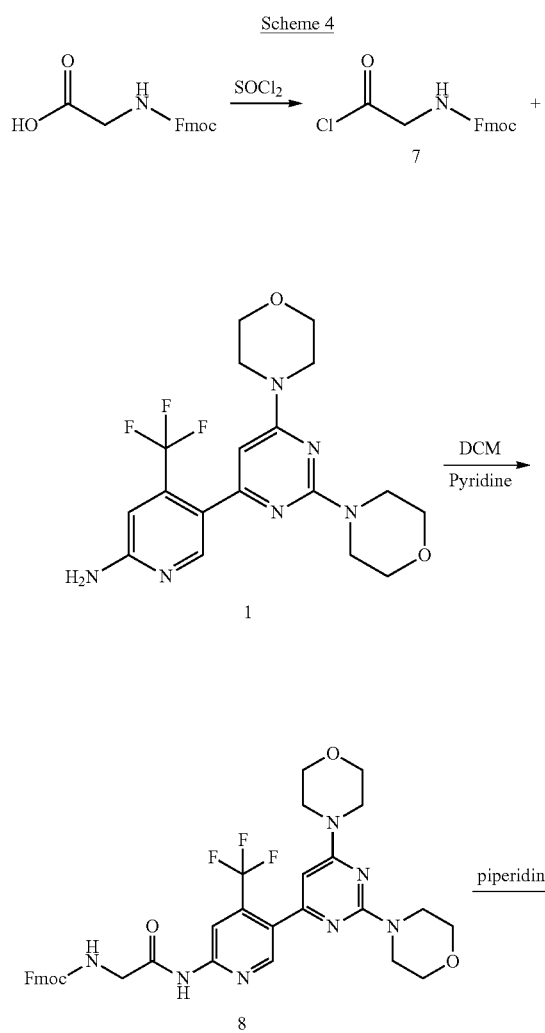

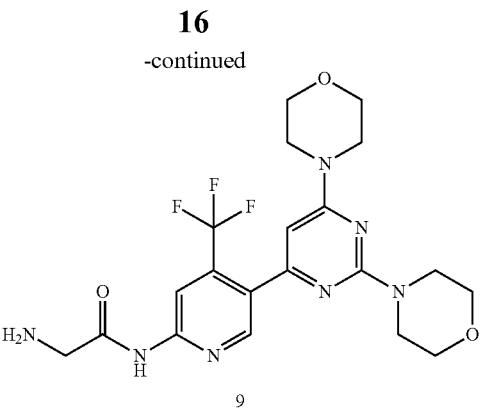

Indication

The present invention provides compounds which are capable of modulating one or more signal transduction pathways comprising, but not limited to PI3 kinases.

By the term "modulating," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Formulations and Method of Use

The amount of compound(s) which is/are administered and the dosage regimen for treating cancer with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Combinations

While the compounds of the invention can be dosed or administered as the sole active pharmaceutical agent, they can also be used in combination with one or more compounds of the invention or in conjunction with other agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formulas I and II is co-administered with a second therapeutic agent, wherein the compound of Formulas I and II and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formulas I and II is initiated prior to, during, or after treatment with a second agent described herein, and continues until any time during treatment with the second agent or after termination of treatment with the second agent. It also includes treatments in which a compound of Formulas I and II and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

The compounds of Formulas I and II as well as combination therapies that include compounds of Formulas I and II, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Specifically, the administration of compounds of the present invention in some embodiments are in conjunction with additional therapies known to those skilled in the art in the prevention or treatment of cancer.

Example 1: The synthesis of N-(5-(2,6-dimorpholinopyrimidin-4-yl)-4-(trifluoromethyl)pyridin-2-yl)acetamide (Compound 2)

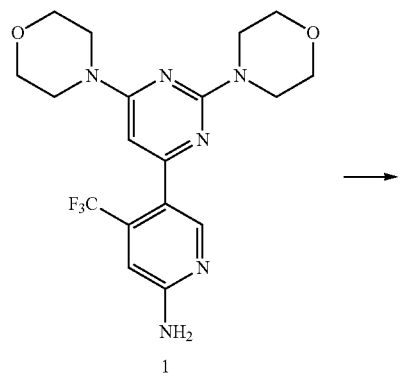

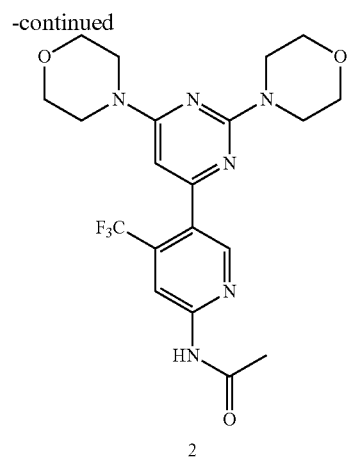

5-(2,6-Dimorpholinopyrimidin-4-yl)-4-(trifluoromethyl)pyridin-2-amine (Compound 1) was prepared according to the literature (WO2007084786 and WO2008098058). To a solution of Compound 1 (100 mg, 1.0 eq) and pyridine (47.4 mg, 2.5 eq) in DCM (5 mL) at 0° C. was added acetyl chloride (28.2 mg, 1.2 eq). The reaction mixture was stirred at 0° C. overnight and TLC indicated the consumption of the starting material. The reaction was quenched with water (20 mL). The aqueous layer was extracted with ethyl acetate (8×20 mL), and the combined organic layers were washed with brine, dried over ($Na_2SO_4$), filtered, and concentrated. The crude product was purified by flash chromatography on silica gel to give the title compound of N-(5-(2,6-dimorpholinopyrimidin-4-yl)-4-(trifluoromethyl)pyridin-2-yl)acetamide 30 mg. $^1$H-NMR ($CDCl_3$): δ8.58 ppm (s, 1H), 8.45 (s, 1H), 8.10 (s, 1H), 5.99 (s, 1H), 3.80-3.74 (m, 12H), 3.62-3.59 (m, 4H), 2.26 (s, 3H). MS m/z 453.7 [M+1].

Example 2: The synthesis of N-(5-(2,6-dimorpholinopyrimidin-4-yl)-4-(trifluoromethyl)pyridin-2-yl)benzamide (Compound 3)

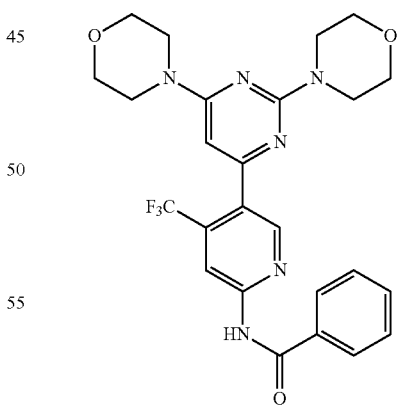

To a solution of Compound 1 (400 mg) in DCM (10 mL) was added pyridine (225 mg, 3.0 eq) at 0° C. The benzoyl chloride (140 mg, 1.05 eq) was added and stirred at 0° C. for 4 hours. Water (20 mL) was added to the reaction. The aqueous layer was extracted with EA (2×10 mL). The combined organic layers were washed with brine (20 mL), dried over anhydrous sodium sulfate, filtered, and concentrated. The crude product was purified by flash column chromatography on silica gel with EA:Hexane (v/v=1:4) to give the title compound as an off-white solid (200 mg). ¹H-NMR (CDCl₃): δ8.81 ppm. (s, 2H), 8.50 (s, 1H), 7.95 (t, J=3.3 Hz, 2H), 7.62 (t, J=3.3 Hz, 1H), 7.54 (t, J=5.7 Hz, 2H), 6.0 (s, 1H), 3.74-3.80 (m, 12H), 3.59-3.62 (m, 4H).

Example 3: The synthesis of 5-(2,6-dimorpholinopyrimidin-4-yl)-N-methyl-4-(trifluoromethyl)pyridin-2-amine (Compound 4)

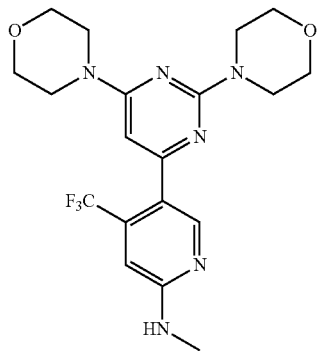 [SMILES: CNc1cc(C(F)(F)F)c(-c2cc(N3CCOCC3)nc(N3CCOCC3)n2)cn1]

To a solution of Compound 1 (1.0 g, 1.00 eq) in DMF (10 mL) was added NaH (192 mg, 2.00 eq) at 0° C. The reaction was stirred 0.5 hour at RT and then iodomethane (203 mg, 0.6 eq) was added. After 10 minutes, water (20 mL) was added to the reaction, the layers were separated and the water layer was extracted with EA (2×50 mL). The combined organic layers were washed with brine (50 mL), dried over anhydrous sodium sulfate, filtered and concentrated. The crude product was purified by column chromatography on silica gel with EA/hexane (v/v=1:2) to give the title compound (150 mg). ¹H-NMR (CDCl₃): δ8.37 ppm. (s, 1H), 6.67 (s, 1H), 6.0 (s, 1H), 3.73-3.79 (m, 12H), 3.58-3.60 (m, 4H), 3.16 (s, 6H).

Example 4: The synthesis of 5-(2,6-dimorpholinopyrimidin-4-yl)-N-ethyl-4-(trifluoromethyl)pyridin-2-amine (Compound 5)

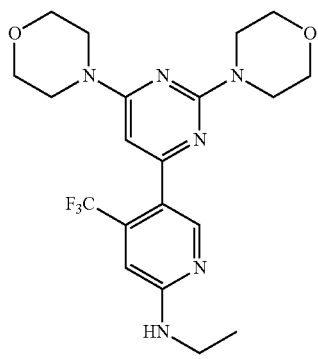 [SMILES: CCNc1cc(C(F)(F)F)c(-c2cc(N3CCOCC3)nc(N3CCOCC3)n2)cn1]

To a solution of Compound 1 (300 mg, 1.0 eq) in DMF (10 mL) was added NaH (70 mg, 2.4 eq) 0° C. The reaction was stirred for 0.5 hour at RT, then iodoethane (135 mg, 1.2 eq) was added to the reaction mixture. After 10 minutes, water (20 mL) was added to the reaction. The layers were separated and the water layer was extracted with EA (2×50 mL). The combined organic layers were washed with brine (50 mL), dried over anhydrous sodium sulfate, filtered and concentrated. The crude product was purified by column chromatography on silica gel with EA/hexane (v/v=1:2) to give the title compound (100 mg). ¹H-NMR (CDCl₃): δ8.29 ppm (s, 1H), 6.64 (s, 1H), 6.0 (s, 1H), 3.73-3.79 (m, 12H), 3.59-3.61 (m, 4H), 3.37-3.39 (m, 2H), 1.45 (t, J=5.4 Hz, 3H).

Example 5: The synthesis of 5-(2,6-dimorpholinopyrimidin-4-yl)-N-propyl-4-(trifluoromethyl)pyridin-2-amine (Compound 6)

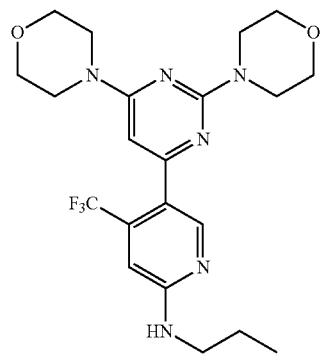 [SMILES: CCCNc1cc(C(F)(F)F)c(-c2cc(N3CCOCC3)nc(N3CCOCC3)n2)cn1]

To a solution of Compound 1 (300.0 mg, 1.0 eq) in DMF (10 mL) was added NaH (70 mg, 2.4 eq) at 0° C. The reaction was stirred 0.5 hour at RT, then iodopropane (150 mg, 1.2 eq) was added to the reaction mixture. After 10 minutes, water (20 mL) was added to the reaction, the layers were separated and the water layer was extracted with EA (2×50 mL). The combined organic layers were washed with brine (50 mL), dried over anhydrous sodium sulfate, filtered and concentrated. The crude product was purified by column chromatography on silica gel with EA/hexane (v/v=1:2) to give the title compound (20 mg). ¹H-NMR (CDCl₃): δ8.28 ppm. (s, 1H), 6.64 (s, 1H), 6.0 (s, 1H), 3.73-3.79 (m, 12H), 3.59-3.61 (m, 4H), 3.29-3.32 (m, 2H), 1.64-1.70 (m, 2H), 1.45 (t, J=5.4 Hz, 3H).

Example 6: The synthesis of 2-amino-N-(5-(2,6-dimorpholinopyrimidin-4-yl)-4-(trifluoromethyl)pyridin-2-yl)acetamide (Compound 9)

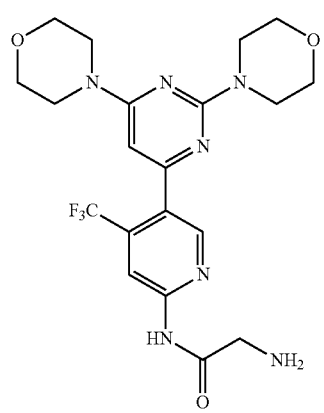 [SMILES: NCC(=O)Nc1cc(C(F)(F)F)c(-c2cc(N3CCOCC3)nc(N3CCOCC3)n2)cn1]

Fmoc-glycine (2.0 g) was dissolved in DCM (8 mL) and THF (2 mL), and SOCl$_2$ (4 mL) was added. The reaction was heated to reflux for 2 hours and the solvent was evaporated in vacuum. The residue was dissolved in DCM and evaporated three times to give Compound 7 as an off-white solid. The crude Compound 7 was dissolved in DCM (10 mL) and added to a mixture of compound 1 (1.13 g, 0.4 eq) and pyridine (1.3 g, 2.4 eq) in DCM (20 mL). The reaction mixture was stirred for 1 hour and the solvent was removed in vacuum. The residue was washed with methanol (2×20 mL), and dried to give Compound 8. To a solution of Compound 8 in DCM (30 mL) was added piperidine (6 mL) at RT. The reaction was stirred 2 hours at RT and TLC indicated completion of the reaction. The reaction mixture was concentrated and the crude was purified by column chromatography on silica gel with DCM/MeOH (v/v=100:1) to give the title compound (240 mg). $^1$H-NMR (CDCl$_3$): δ10.12 ppm (s, 1H), 8.66 (s, 1H), 8.49 (s, 1H), 6.00 (s, 1H), 3.80-3.75 (m, 12H), 3.62-3.52 (m, 6H). MS m/z 468.5 [M+1].

Example 7: The synthesis of (R)-2-amino-N-(5-(2,6-dimorpholinopyrimidin-4-yl)-4-(trifluoromethyl)pyridin-2-yl)propanamide (Compound 10)

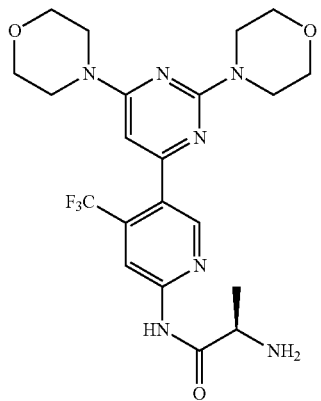 [SMILES: C[C@@H](N)C(=O)Nc1cc(C(F)(F)F)c(-c2cc(N3CCOCC3)nc(N3CCOCC3)n2)cn1]

Compound 10 is prepared using Fmoc-(R)-2-aminopropanoic acid as the starting materials following a similar procedure that described for the synthesis of compound 9. MS m/z 482 [M+1].

Example 8: The synthesis of (S)-2-amino-N-(5-(2,6-dimorpholinopyrimidin-4-yl)-4-(trifluoromethyl)pyridin-2-yl)propanamide (Compound 11)

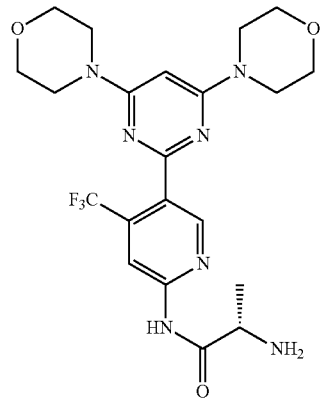 [SMILES: C[C@H](N)C(=O)Nc1cc(C(F)(F)F)c(-c2nc(N3CCOCC3)cc(N3CCOCC3)n2)cn1]

Compound 11 is prepared using Fmoc-(S)-2-aminopropanoic acid as the starting materials following a similar procedure that described for the synthesis of compound 9. MS m/z 482 [M+1].

Biological Assays:

As stated hereinbefore, the compounds defined in the present invention possess anti-proliferation activity. These properties may be assessed, for example, using one or more of the procedures set out below:

(a) An in vitro assay which determines the ability of a test compound to inhibit PI3K alpha activity: PI3 alpha (PIK3CA) kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Most K$_d$'s were determined using a compound top concentration=30,000 nM. If the initial K$_d$ determined was <0.5 nM (the lowest concentration tested), the measurement was repeated with a serial dilution starting at a lower top concentration. A $K_d$ value reported as 40,000 nM indicates that the $K_d$ was determined to be >30,000 nM.

Binding constants ($K_d$'s) were calculated with a standard dose-response curve using the Hill equation: Response=Background+(Signal−Background)/(1+ ($K_d^{Hill\ Slope}$/Dose$^{Hill\ Slope}$)) The Hill Slope was set to −1. Curves were fitted using a non-linear least square fit with the Levenberg-Marquardt algorithm.

(b) An in vitro assay which determines the ability of a test compound to inhibit PI3K delta. The assay was performed under a similar condition to the one that has been described above for (a) An in vitro assay which determines the ability of a test compound to inhibit PI3K alpha activity, except that the following enzyme PI3K delta was used.

(c) An in vitro assay which determines the ability of a test compound to inhibit MTOR (Mammalian target of rapamycin). The assay was performed under a similar condition to the one that has been described above for (a) An in vitro assay which determines the ability of a test compound to inhibit PI3K alpha activity, except that the following enzyme MTOR was used. Compound 9 has $IC_{50}$=26 nM for MTOR inhibition.

The following Table A lists compounds representative of the invention and their activities in PI3K alpha assay.

TABLE A

| Compound | PI3K alpha ($IC_{50}$) |
| --- | --- |
| 2 | 0.4 nM |
| 4 | 1.9 nM |
| 5 | 10 nM |
| 6 | 60 nM |
| 9 | 0.84 nM |

The following Table B lists compounds representative of the invention and their activities in PI3K delta assay. Compound 2 ($IC_{50}$=32 nM) has much better activity against PI3K delta than Compound 1 ($IC_{50}$=310 nM).

TABLE B

| Compound | PI3K delta ($IC_{50}$) |
| --- | --- |
| 1 | 310 nM |
| 2 | 32 nM |

A representative number of compounds were assayed against MCF-7 human breast cancer cell lines using the cell proliferation assay:
1. MCF-7 cells were cultured in EMEM (GIBCO, Cat#41500) medium supplemented with 10% fetal bovine serum, 0.01 mg/ml human recombinant insulin and 1% penicillin-streptomycin solution, in the temperature of 37° C., 5% $CO_2$ and 95% humidity. The cells were harvested during the logarithmic growth period and counted with hemocytometer. The cell viability will be over 98% by trypan blue exclusion. Cell Counting Kit-8 (Dojindo, Cat# CK04) was used.
2. A cell suspension (100 μl) was added into 96-well plates (triplicates for each cell concentration), the cell density was $4.0 \times 10^3$/well. The next day, the test articles or positive drug stock solution were dissolved in DMSO at the concentration of 10 mM, the stock solutions were diluted with DMSO by serial 3 or 10 fold dilution. Then the test articles dilutions were further diluted with culture medium to the final concentrations of (10.0 μM, 3.33 μM, 1.11 μM, 366 nM, 122 nM, 40.7 nM, 13.6 nM, 4.52 nM and 0 nM), the positive drug dilutions were further diluted with culture medium to 9 final concentrations of (10 μM, 1 μM, 100 nM, 10 nM, 1 nM, 0.1 nM, 0.01 nM, 0.001 nM and 0 nM). One hundred microliter of drug solution was dispensed into each well, the cells then were cultured for another 72 hours. The WST-8 solution was prepared immediately prior to use, the culture medium and the drug solution was removed, and 100 fresh medium with 10 μl of the cck-8 buffer (WST-8) was pipetted to each well. The plate was incubated for 2 hours at 37° C. in a humidified, 5% $CO_2$ atmosphere. The absorbance was recorded at 450 nm using Victor Multilabel Plate Reader.

The data was displayed graphically using GraphPad Prism 5.0. To calculate IC50, a dose-responsive curve was fitted using nonlinear regression model with a sigmoidal dose response. The IC50 was automatically produced by Graph-Pad Prism 5.0.

The surviving rate(%)=($OD_{Test\ article}$−$OD_{Medium\ control}$)/($OD_{None\ treated}$−$OD_{Medium\ control}$)×100%.

The following Table C lists compounds representative of the invention and their activities in MCF-7 cell assay.

TABLE C

| Compound | MCF-7 cell assay ($IC_{50}$) |
| --- | --- |
| 1 | 186.4 nM |
| 2 | 82.4 nM |

In Vivo Xenograft Assay:

A representative protocol for the in vivo experiment is as follows to establish the subcutaneous A549 cell line xenograft model in nude mice and to evaluate the in vivo therapeutic efficacy of the compounds: A549 cells were cultured in RPMI1640 containing 10% fetal bovine serum, 1% L-glutamine, 100 U/mL penicillinG and 100 μg/mL streptomycin. Cells in logarithmic growth phase were harvested and resuspended in 1×PBS for implantation.

Tumor xenografts were established by injecting tumor cells $5 \times 10^6$/mouse into the right flank by sc under sterile conditions. When the tumors reached an appropriate size (100-200 mm$^3$), mice were randomized into 6 mice per group (8 mice in control group). The tumors were measured using a caliper in two dimensions, length (a), and width (b). Tumor volumes were estimated from measurements of two diameters of the individual tumors as follows:

Tumor Volume(mm$^3$)=$(a \times b^2)/2$

The tumor sizes and animal body weights were measured twice a week. Mice were observed daily for clinical signs. Blood samples were collected 2 hours after last treatment; plasma samples were prepared and stored at −80° C. Tumor tissues were separated, weighed, taken picture, and subsequently stored at −80° C. for further analysis. All animal experiments were performed in accordance with the Guidelines for Use and Care of Animals of the University of Traditional Medicine. The parameters for in vivo efficacy evaluation were calculated according to the guidance of SFDA. Percent T/C (%) was calculated with the following formula: T/C(%)=($T_{RTV}$/$C_{RTV}$)×100%, where $T_{RTV}$ and $C_{RTV}$ stand for relative tumor volume in treatment group and vehicle control group, respectively. Relative tumor volume (RTV) was calculated using the formula: RTV=Vt/$V_0$, where Vt represents volume on testing day, and $V_0$ represents volume on first day of treatment. Tumor growth inhibition (TGI, %) were calculated as TGI (%)=($C_{tw}$−$T_{tw}$)/$C_{tw}$×100%, where $C_{tw}$ and $T_{tw}$ represent mean tumor weight in vehicle control and treatment group, respectively.

Compound Preparation: Test articles were dissolved in 100% N-methylpyrrolidone (NMP) and 10× solutions were prepared every five days, aliquotted, and stored in the dark at room temperature. On each treatment day, stock solution aliquots were diluted with polyethylene glycol (PEG300) to provide the formulated drug in 10% NMP: 90% PEG300. Dosing solutions were protected from light, and the formulated drug was administered within 1 hour after preparation. In all groups, the dosing volume of 10 mL/kg (0.2 mL/20 g mouse) was scaled to the weight of each animal as determined on the day of dosing, except on weekends when the previous BW is carried forward. Test articles were administered by oral gavage (p.o.) once daily until the end of the study.

At study endpoint, after blood collection, mice were practiced euthanasia by cervical dislocation, the tumor tissue was collected first, then abdominal cavity was cut open, liver and spleen were excised, then weight after the gallbladder was removed respectively. Organ weight between the treated versus the control groups were compared.

The following Table D lists compounds representative of the invention and their activity in subcutaneous A549 cell line xenograft model in nude mice described above. Compound 1 or Compound 2 was dosed at 49 μmol/kg and 98 μmol/kg by oral gavage once daily for numbers of days. Tumor growth inhibition (TGI, %) was calculated. At day 14, Compound 2 showed better inhibition than Compound 1 both at 49 μmol/kg (52% vs. 36%) and at 98 μmol/kg (82% vs. 70%).

TABLE D

In vivo A549 xenograft model Tumor growth inhibition (TGI, %) at 14 days.

| Doses | Compound 1 | Compound 2 |
|---|---|---|
| 49 μmol/kg | 36% | 52% |
| 98 μmol/kg | 70% | 82% |

The following Table E lists compounds representative of the invention and their activities and kidney changes in subcutaneous A549 cell line xenograft model in nude mice described above. At day 21, Compound 9 showed better efficacy than Compound 1 at 49 μmol/kg dose. Compared with the control, Compound 9 had much less decreased kidney weight than Compound 1, which indicated a much better safety profile.

TABLE E

In vivo A549 xenograft model Kidney weight changes compared to the control at 21 days.

| Dose | Kidney weight change of Compound 1 | Kidney weight change of Compound 9 |
|---|---|---|
| 49 μmol/kg | −8.7% | −5.0% |
| 98 μmol/kg | −20.1% | −8.1% |

What is claimed is:

1. A compound or its pharmaceutically acceptable salt, or solvate thereof selected from the group consisting of:

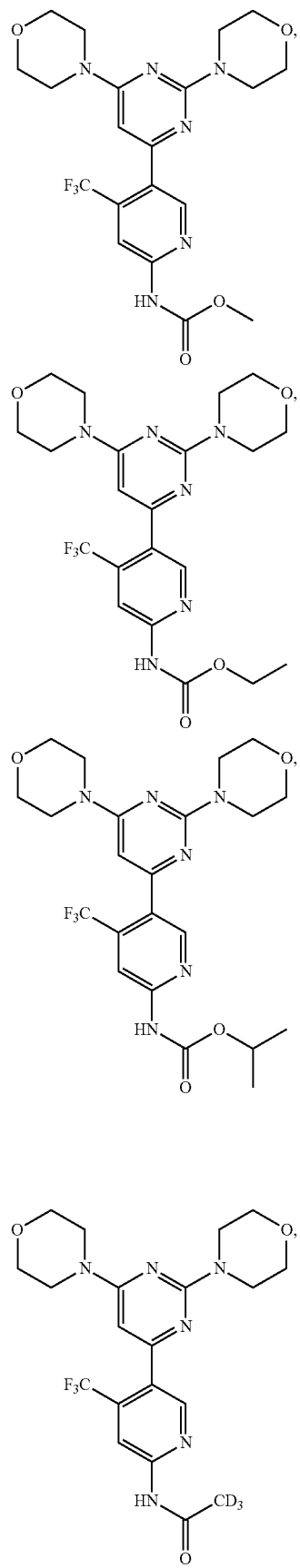

-continued
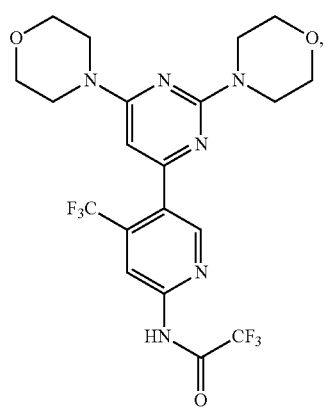
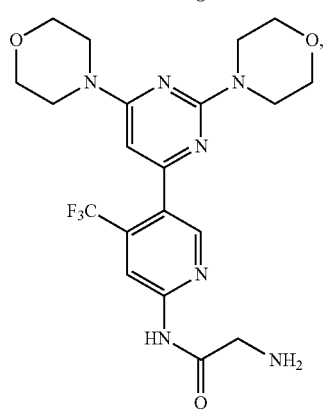
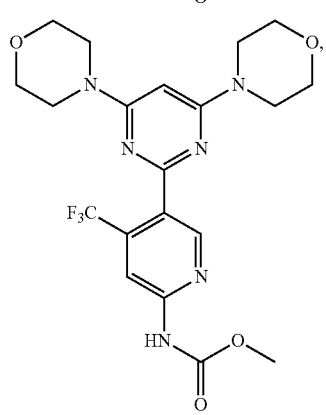
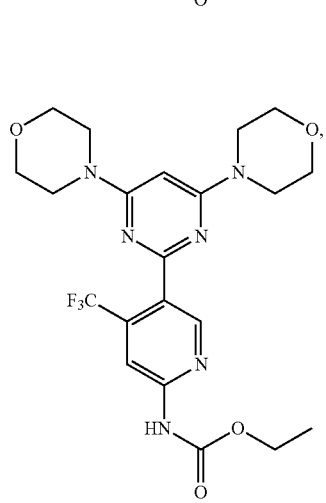
-continued
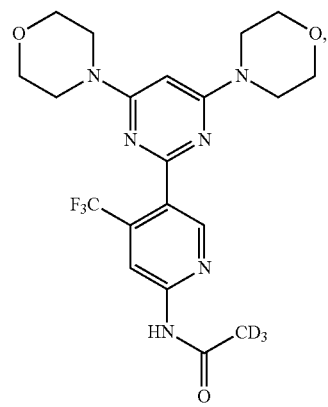
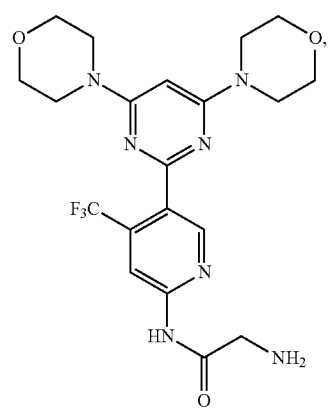
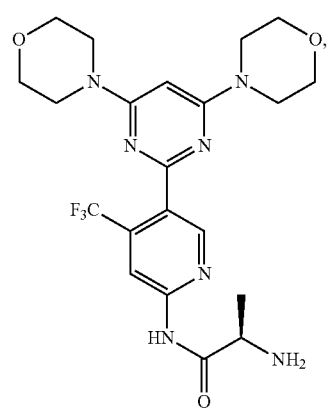

31
-continued
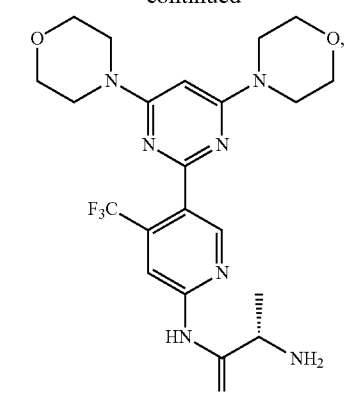
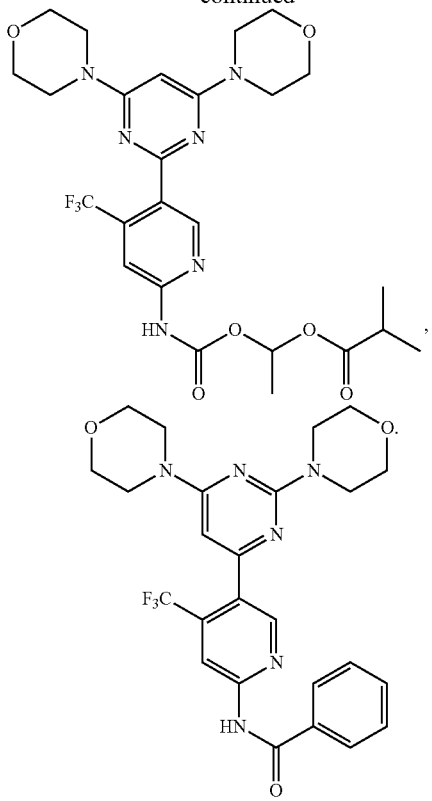
32
-continued
* * * * *